United States Patent [19]

Artal

[11] Patent Number: 5,406,961
[45] Date of Patent: Apr. 18, 1995

[54] MONITORING DEVICE AND METHOD FOR DETECTION OF PREMATURE LABOR

[76] Inventor: Raul Artal, 6927 Kassonta Dr., Jamesville, N.Y. 13078

[21] Appl. No.: 145,763
[22] Filed: Oct. 29, 1993
[51] Int. Cl.⁶ .............................................. A61B 5/00
[52] U.S. Cl. ...................................... 128/778; 128/774
[58] Field of Search ................. 607/62, 138; 128/774, 128/778, 834, 839

[56] References Cited

U.S. PATENT DOCUMENTS

| | | | |
|---|---|---|---|
| 3,474,776 | 10/1969 | O'Brien | 128/839 |
| 4,909,263 | 3/1990 | Norris | 128/778 X |
| 4,942,882 | 7/1990 | Bellinson | 128/778 X |
| 4,966,101 | 10/1990 | Wallace et al. | 128/778 X |
| 4,989,615 | 2/1991 | Hochberg | 128/778 X |
| 5,154,177 | 10/1992 | Elsman et al. | 128/778 X |
| 5,167,237 | 12/1992 | Rabin et al. | 128/778 X |

*Primary Examiner*—Sam Rimell
*Attorney, Agent, or Firm*—Hawes & Fischer

[57] ABSTRACT

A pessary senses the dilation and effacement of the cervix of patients at risk for premature labor by sensing changes in the energy levels transmitted through the cervical tissue. In one embodiment, light is utilized to periodically illuminate tissues adjacent the cervix, the light being detected serving as an indicator of the onset of labor. The detection of a condition of premature labor is transmitted to a patient monitor through either conductors extending out of the body and into the monitor, or via electromagnetic transmissions (radio) sent from the pessary to a receiver associated with the patient monitor. Interpretation of the energy detected may occur either within the pessary or within the patient monitor.

15 Claims, 5 Drawing Sheets

MONITORING DEVICE AND METHOD FOR DETECTION OF PREMATURE LABOR

FIELD OF THE INVENTION

The present invention relates to the field of medical devices. More specifically, the present invention relates to a system and method for early detection of premature labor via the measurement of cervical dilation and effacement and is particularly useful for individuals at risk for premature labor.

BACKGROUND OF THE INVENTION

There are certain individuals which are subject to premature labor which can result in either a premature birth or miscarriage. The state of premature labor can be corrected via the use of drugs known as tocolytics and the provision of immediate medical care. However, the premature labor state by and large cannot normally be identified by the patient so as to enable medical help to be sought at the time of such premature labor. The ability of a patient to identify the onset of premature labor and immediately seek medical attention will significantly reduce the instances of premature birth and miscarriage.

Premature birth requires 24-hour per day monitoring of the prematurely born child, at a cost on the order of thousands of dollars per day. Such monitoring usually continues until the child is of sufficient birth weight and sufficiently healthy that he can be discharged, which can require months.

In as many as 45% of the instances of premature birth, silent labor occurs where the onset of dilation, effacement and change in orientation of the cervix occurs without the accompaniment of perceived uterine contractions until perhaps minutes before delivery. Conversely, false labor may occur, including the onset of uterine contractions without dilation or effacement of the cervix.

Further, the ability to determine the extent to which premature labor is occurring can be of immeasurable help to the medical practitioner. The dosage of medication and type of treatment will depend upon the extent to which the premature labor process has progressed. The medication will typically be a tocolytic agent, such as terbutaline, ritodrine, and magnesium sulfate.

Once the cervix has dilated to a dimension in excess of four centimeters, the labor process will have begun in earnest and is not subject to reversal. Therefore the onset of labor must be detected, usually within an hour of its beginning, to have a significant chance of preventing such premature labor.

The use of a pessary has been known for some time. The dictionary definition of pessary is "a device worn in the vagina to support a displaced uterus." A modern day pessary type device is the diaphragm. Diaphragms are typically disks each having a curved continuous edge, typically supported with an internal wire spring.

The current use of a pessary for supporting a displaced uterus has been replaced by surgical procedures.

In other specialized circumstances, a pessary may be prescribed by an obstetrician, such as for the promotion of healing of trophic cervical lacerations, the relief of acute urinary retention due to a retroposition of the uterus in mid-pregnancy, preventing or relieving postpartum subinvolution or retroversion, or to protect against spontaneous abortion in the case of cervical incompetence.

Since the use and utility of the pessary has been proven, and since it lies in a position proximate to the cervical opening, what is needed is a method to use the pessary to indicate the onset of premature labor.

What is needed is a pessary which can be pre-selected to fit different sizes of vaginal canals and cervical sizes, but which does not touch or irritate the cervix or vagina. The pessary should not block the area of the os, and should be made of a material which will not cause a reaction in the vaginal/uterine environment. The device should be smooth, and should be constructed to facilitate insertion and removal.

The methods employed in detecting the onset of premature labor should not register false positive labor indications despite patient movement and normal non-vigorous activities. The needed structure must be available in sterile form and be sterilizable. It should also be amenable to an operating mode which will conserve battery power.

SUMMARY OF THE INVENTION

The method and device of the present invention enables the use of a pessary to sense the dilation and effacement of the uterus. The sensing of such dilation and effacement can occur via the use of a single frequency of light generated intermittently on one side, or end, of the pessary and detected by the other side, or end, of the pessary. During the labor process, the dilation and effacement of the lower part of the uterus causes tissues in that region to extend and become less thick and less vascular. Such thinning of the tissues will make them more susceptible to the transmission of electromagnetic energy.

The detection of such electromagnetic energy on the other end, or side, of the pessary, after attenuation by the cervical tissue, is an indicator of the condition of the cervix. The electromagnetic energy could be from a light emitting diode, or of radio frequency, or any other form of energy which would be attenuated based upon the condition of the cervical tissue. The detection of the change in the cervix could be detected and transmitted to a point outside the body in real time. In addition, the changes could be recorded in a memory chip on the pessary for accessing at a later time where it is important to obtain historical data, or data relating to the timing of the changes in the cervix leading up to the onset of premature labor. Such information could also be stored within a patient monitor for playback as needed. Knowing the sequence and speed with which indicia of premature labor occurred would enable the physician to re-set an alarm signal in the patient monitor so that any subsequent premature labor cycle could be detected sooner.

The manner in which signals from the detector on the pessary can be transmitted to the patient monitor are many. Extremely small data wires could be extended from the pessary to a patient monitor. Another possibility would be the use of microwave and higher frequencies for radio telemetry from a small transmitter on the pessary directly to a receiver located at the patient monitor.

The design of such a transmitter system would be done with due consideration to the power consumption required, the sensitivity of the receiver, and the expected proximity of the receiver to the pessary transmitter. In some instances, the patient monitor and pessary transmitter may be set to alarm only if the cervical changes were to proceed beyond a pre-set limit. In other instances, the pessary transmitter could be set to relay signals to the patient monitor intermittently so as to record a cervical change history for future reference. Alternatively, the rate of information transfer may be speeded up upon detection of cervical activity.

BRIEF DESCRIPTION OF THE DRAWINGS

The invention, its configuration, construction, and operation will be best further described in the following detailed description, taken in conjunction with the accompanying drawings in which:

FIG. 7 is a block schematic illustrating one configuration in which the energy emitters and sensor components of the present invention may be connected and controlled.

DETAILED DESCRIPTION OF THE PREFERRED EMBODIMENT

Figure 1:
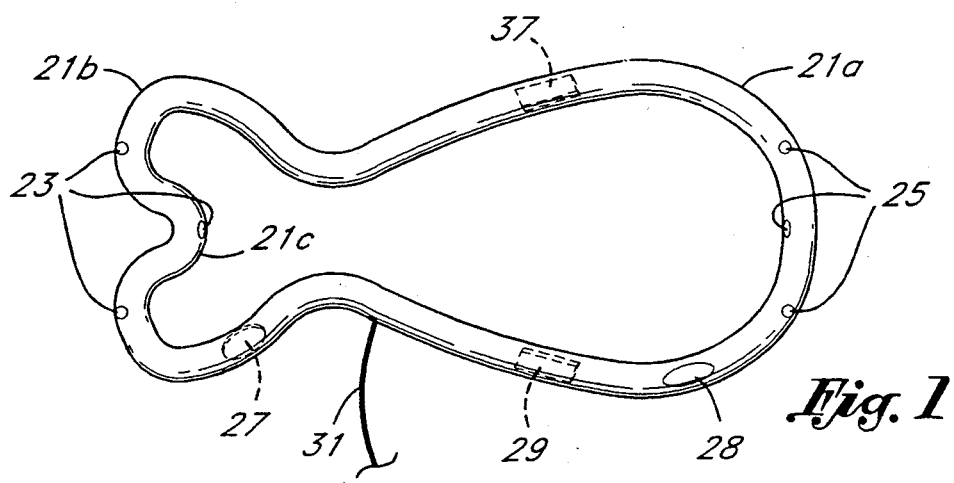
FIG. 1 is a plan view of one possible configuration of a pessary utilizable in conjunction with the device and method of the present invention.
Figure 2:
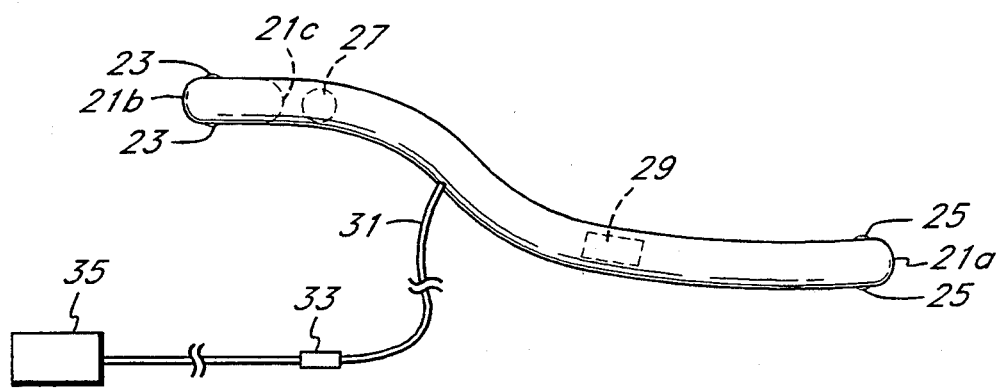
FIG. 2 is a side view of the pessary shown in FIG. 1 and illustrating that one end of the pessary of the present embodiment lies in an elevated plane with respect to the other end.

The description and operation of the invention will be best initiated with reference to FIGS. 1 and 2. FIG. 1 is a plan view of a pessary 21, while FIG. 2 is a side view of pessary 21. It is understood that the pessary 21 shown is but a single possible configuration for use as a monitoring platform to detect the onset of premature labor. The pessary 21 is shaped as a loop having a larger loop and more gently curved end 21a, and a smaller loop and more sharply curved end 21b. End 21b further includes a small indentation 21c at its midpoint to prevent blockage of the urethra. The internal surface of the pessary 21 may have a somewhat frusto-conical annular surface to more readily fit the lower section of the cervix 21 about which it resides, as will be shown. The pessary 21 is preferably made of soft, pliable material. The diameter of the pessary 21 will nominally have a dimension of about 70.0 millimeters at the maximum diameter (between the ends 21a and 21b), and a dimension across its width of about 35 millimeters. It is contemplated that the pessary 21 will be available in a variety of sizes of average diameter, usually ranging from about 90.0 millimeters to about 50.0 millimeters. The availability of a variety of sizes is desirable to make a good fit with a particular size of vaginal canal and cervical opening into which the pessary 21 is to be placed.

Referring to FIG. 2, the side view of the wall of the pessary 21 at the top and bottom shows a vertical thickness of about 5.0 millimeters. The cross sectional area of the pessary 21 is not shown, but it may have a cross section defining an inwardly directed frusto-conical surface to match the outer surface of the cervix (to be shown) which the pessary 21 will lie adjacent. The pessary 21 may have a thin wall, or a somewhat more thick wall depending upon the electronics and other structures which it needs to support.

Indeed, variations in the general shape of the pessary 21 are contemplated, including having the planes of the top and bottom profile of the pessary 21, especially as shown in FIG. 2, to include a non parallel shape. In other words, the pessary 21 may be vertically thicker at one end than at the other end. The same may be true for vertical thickness at the sides versus vertical thickness at the ends. Further, the pessary 21 may be circular. It may be oval, or it may have any other shape which will increase the likelihood of its staying in place within the patient. Finally, the pessary 21 may be custom made to fit a particular patient.

A variety of structures may be mounted within the thickness afforded by the pessary 21. Such structures are shown diagrammatically in FIGS. 1 and 2, and may, in practice, take on differing shapes and locations. One or more energy emitters 23, such as sound producers, or light emitting diodes, are shown as small round circles, may be located at one end of the pessary 21, while one or more detectors 25, typically sound detectors, or light detectors where the energy emitters 23 are light emitting devices, may be located on preferably an opposite end of pessary 21. The direction, in terms of upper or lower side, in which the energy emitters 23 and detectors 25 are located may vary, and indeed, both the energy emitters 23 and detectors 25 may be placed on both the upper and lower sides of the pessary 21.

A small battery 27 may be located in the pessary 21. Battery 27 may likely occupy a naturally rounded space within the pessary 21. Ideally, pessary 21 may be built to be disposable, thus eliminating any need to utilize commonly available batteries, along with the need to either conform an area of the pessary 21 to the shape of a commercially available battery, or to be limited in power due to size and shape considerations regarding size limitation requiring the use of commercially available batteries of a size smaller than would normally otherwise be used.

Several operating modes can be applied to conserve the battery 27. One method involves an intermittent triggering, having a time spacing of from five to ten minutes. In this mode, power would be needed for a clock, but all other circuitry which battery 27 serves could be shut down during the five to ten minute rest period. Another method contemplates the use of a temperature switch 28, shown as a bimetal contact, capable of disconnecting the battery 27 from other circuitry when the temperature of the pessary is below body temperature. This technique would permit the battery 27 to be installed in the pessary 21 at the time of assembly, and would permit the pessary 21 to have a shelf life limited by the battery 27's open circuit shelf life. Due to the thin profile of the pessary 21, the temperature which any such temperature switch experiences should require little time to achieve.

A microchip 29 is shown extending partially about the pessary 21. Microchip 29 may be a microprocessor, or simply a detector amplifier and transmitter. In instances where fine wires are to extend from the pessary to points outside of the body, power can be supplied by a unit to be worn outside of the body, and thus eliminate the space and power limitations which would be encountered in the event that a battery 27 was to be used.

Such optional wiring is shown in FIGS. 1 and 2 as fine wire bundle 31. The possibility of ascending infection should be considered if the use of a pessary 21 having wires is contemplated. Where the need for greater power and more data is paramount, the possibility of using such an externally wired unit must be considered, along with steps to be taken to avoid infection.

The wire bundle 31 would be sealed so that fluids could not enter the spaces within the pessary 21. A connector 33 would most likely be located at the end of the wire bundle 31 opposite the pessary 21, to enable the patient to more easily handle a connected patient monitor unit 35. The patient monitor unit 35 may be of several different types, depending on the expected needs and characteristics of the patients. Most of the devices will be wireless in order to avoid ascending infection.

For example, where silent labor is a noted tendency, monitoring of a much closer nature may be called for. The patient monitor unit 35 may have a memory, liquid crystal output showing a graphical representation of dilation and effacement, and other features. The use of a microprocessor in the patient monitor unit will permit the computation of an array of characteristics for use and analysis. Such characteristics, or parameters may include the magnitude of the change in cervical thickness, the change of cervical thickness per unit time, the slope of the change of cervical thickness per unit time, chemical changes in the vaginal/cervical environment, temperature, uterine motion, tissue color, the frequency of contractions and other aspects relating to the monitoring of cervical changes.

Other monitoring sensors may be mounted within the pessary 21, and which are not shown, and may include a blood velocimeter and perfusion monitor, amniotic fluid turbidity monitor, a fetal heart monitor, a stress monitor to detect change in strain accompanying movement of the cervix accompanying the onset of labor, a sound detector for detecting the sounds accompanying movement, and a sound generator/detector to detect the differing propagation of sound through the cervical tissue as it changes.

A sound transmitter/detector can measure several aspects of the cervical environment. It can measure the distance to the chorio-amniotic membrane through cervical tissue and the vaginal fault. It can measure the increase in diameter of the external cervical os and cervical canal. It can measure the increase in diameter of the internal cervical os and cervical canal. It can measure the decrease in length of cervical canal and cervical tissue, especially due to effacement. It can measure the increase in the volume of air space present, and can detect leaking amniotic fluid. Further, it can measure indicia which indicate the state of all of the above conditions either singly or in combination with other aspects to be measured.

The energy emitters 23 may be turned on intermittently, since only a very short time is required to measure attenuation of light, or other energy, passing through tissue. Further, if the light emitting diodes are of differing wavelength, an analysis of blood constituents may be possible due to the differing absorption of tissue, and especially blood, of light wavelengths. Such techniques are well known in pulse oximetry to determine the percent level of oxygen in the blood, for example.

One possibility for the pessary 21 would be the use of a somewhat flexible circuit board material with circuitry plating for interconnection of the battery 27, microchip 29, and a portion of its plating utilizable as an antenna. Other possibilities for the pessary 21 would be a series of micro strain sensors 37 shown in FIG. 1. Such micro strain sensors 37 can be configured to detect stress in several different directions, even though located at a common site. Much will depend upon how the micro strain sensors 37 are oriented and how they are attached to internal structures in the pessary 21.

Figure 3:
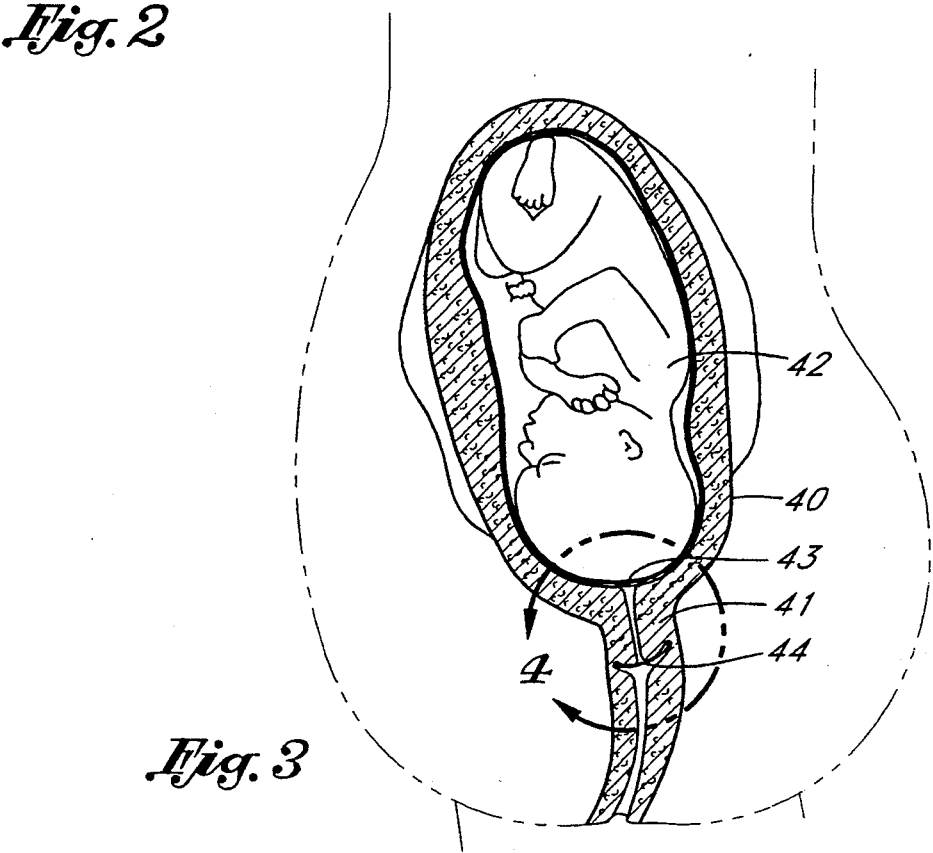
FIG. 3 is a side sectional detail of the female uterus and cervix during pregnancy.

Referring to FIG. 3, a side sectional view of the uterus 40 and cervix 41 as it would appear during pregnancy. The unborn child 42 rests in an inverted position over the internal cervical os 43. The external cervical os 44 is also seen at the lower end of the cervix 41.

Figure 4:
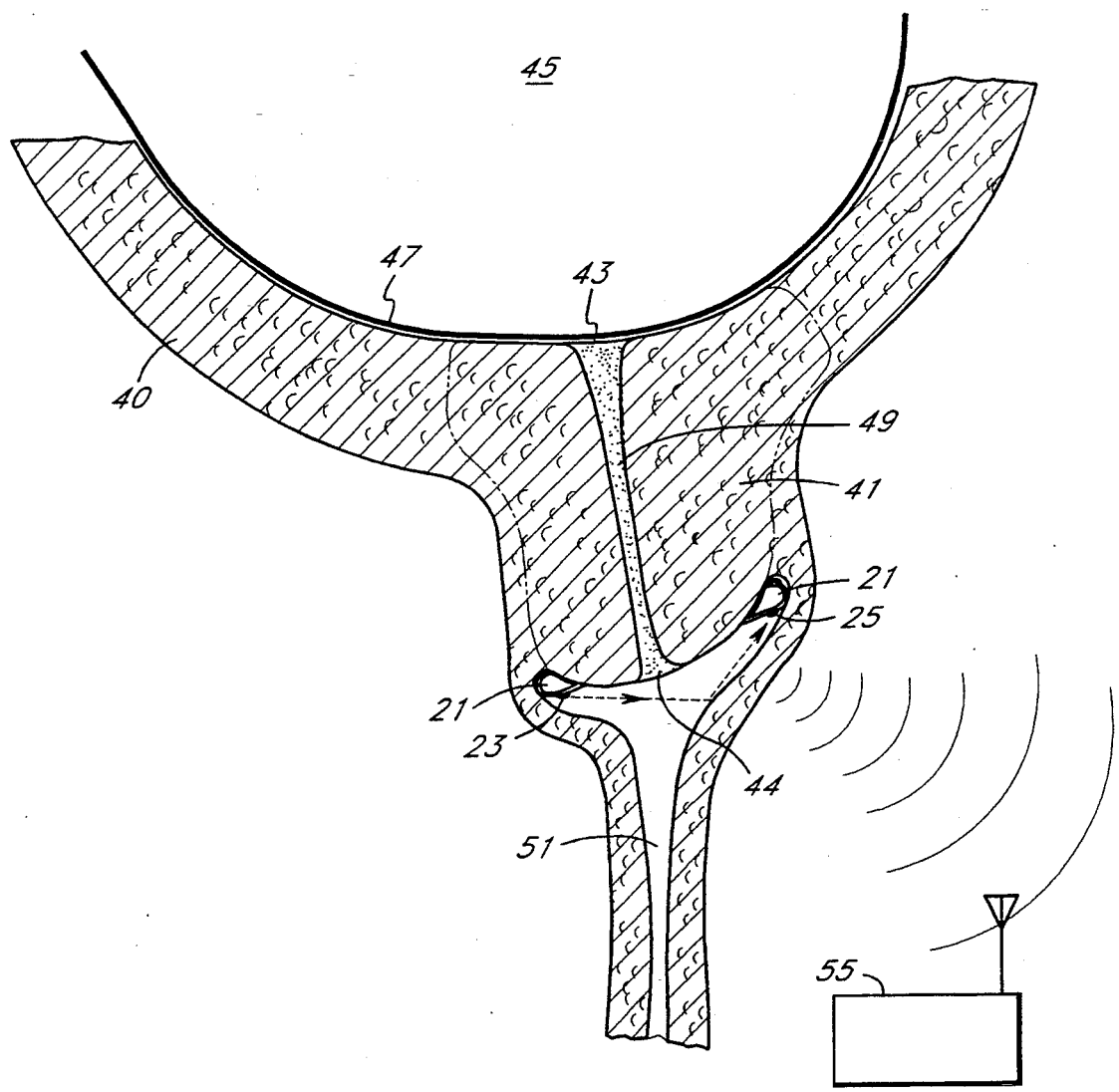
FIG. 4 is a side sectional expanded detail of the female uterus and cervix, as was shown in FIG. 3, before the onset of premature labor.

Referring to FIG. 4, an enlarged detail of a portion of the area shown in FIG. 3 and indicated with a double arrowed circle as view 4—4 is shown. The unborn child 42 is omitted from FIG. 4 and following, for simplicity. In the upper region 45 is the amniotic fluid contained by a membrane sack 47. At the center of the cervix 41 is a mucus plug 49. The vagina 51 is shown having a somewhat narrow width in the lower portion of FIG. 4, but widening at the approach to the cervix 41. The vaginal channel extends partially around the end of the cervix 41, enabling the pessary 21 to encircle this portion of the cervix 41. The cervix 41 and pessary 21 are shown in sectional view.

The state of the cervix 41 as depicted in FIG. 4 is at the stage of normal pregnancy, before the onset of premature labor. In this configuration, the pessary 21 is shown as outputting a radio signal, represented by the curved lines to a patient monitor unit 55 containing radio receiver electronics. The manner in which the signal is transmitted may widely vary depending upon the power output required and the level of monitoring required.

Higher power requirements may dictate the use of the electrically connected pessary 21 shown in FIGS. 1 and 2. Also shown in FIG. 4, in a somewhat oversimplified schematic fashion is the emanation of energy from the energy emitters 23 which makes its way to the detectors 25. Although shown in the format of a reflected arrow, it is understood that, especially in the case where light is used, that the illumination would bathe the tissue area located adjacent and across the internal perimeter of the pessary 21, and that some scattering and reflection due to surrounding tissues would occur.

Again assuming a light energy emitter 23, the amount of light admitted to the detectors 25 will predominantly depend upon the initial light intensity, the attenuation through the cervical tissue, and the shape, thickness and orientation of the cervical tissue. If sound transmitters and detectors were utilized, the sound attenuation both total and with respect to individual frequency components would depend upon the shape and orientation of tissues which are in the vicinity of the pessary 21.

Figure 5:
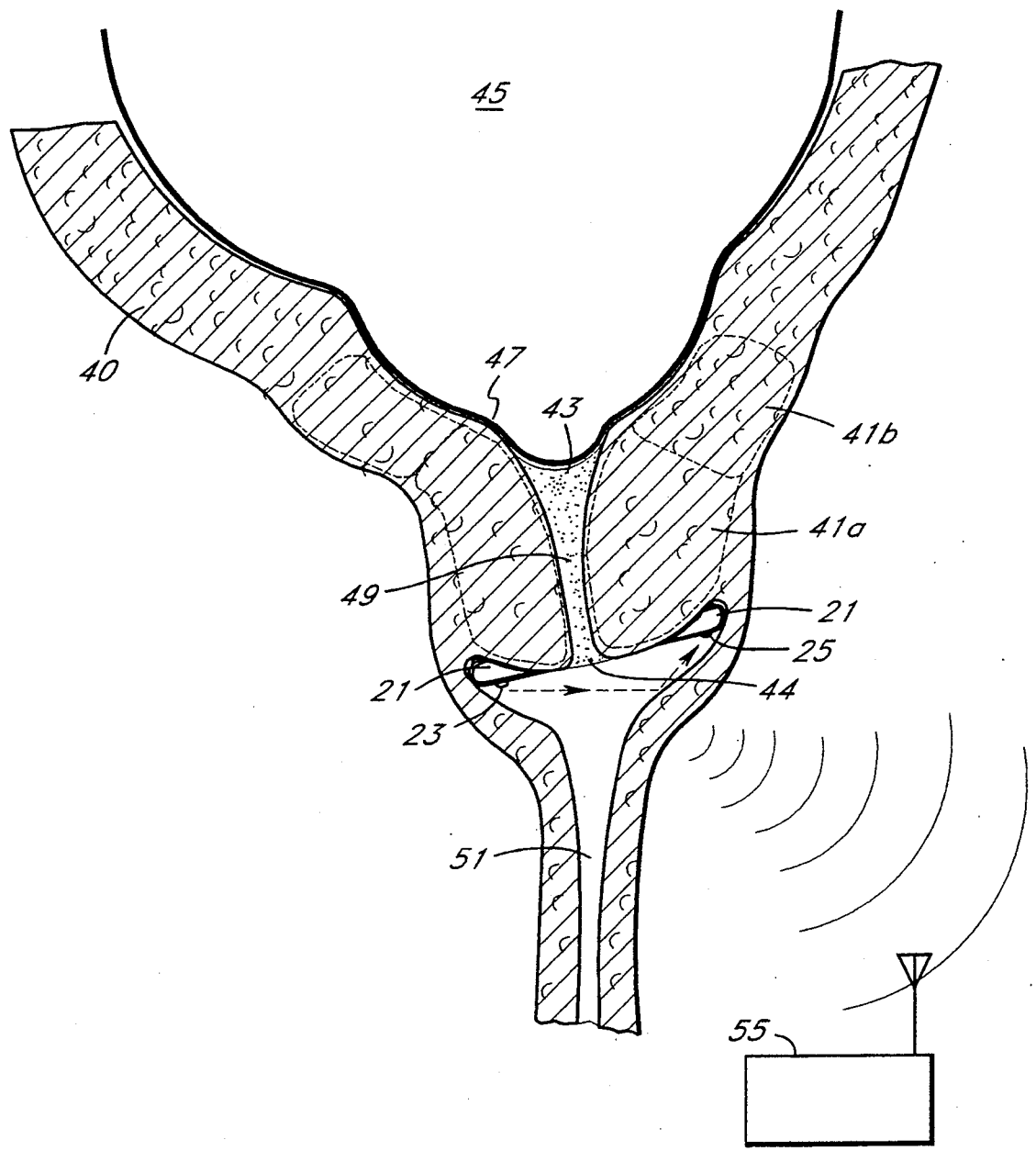
FIG. 5 is a side sectional expanded detail of the female uterus and cervix, as was shown in FIG. 4, but illustrating the onset of premature labor.

Referring to FIG. 5, a view similar to that shown in FIG. 4 illustrates the state of the cervix 41 and uterus 40 during the onset of premature labor. First notice the membrane sac 47 and how it begins to be displaced into an area occupied by the mucus plug 49. The cervix 41 begins to be partially stretched into a stretched cervical region 41b, which can be distinguished from an un-stretched cervical region 41a.

The presence of the stretched region 41b, with less blood perfusion will affect any energy emanating from the energy emitter 23 as it falls on the detector 25. It is during this onset of premature labor that the stress levels within the pessary 21 would be significantly changed from those existing in the conditions as shown in FIG. 4. Micro-stress sensors 37 which were depicted as a cutaway block in FIG. 1 would be incorporated to measure such changed and changing stress occurring at the onset of premature labor.

Note that the lower extreme of the cervix 41a is somewhat more withdrawn beyond the planar limit of the pessary 21 than was the case shown in FIG. 4. Such slight withdrawal gives a significant change in the amount of light which would emanate from the energy emitter 23 as it falls on the detector 25.

Figure 6:
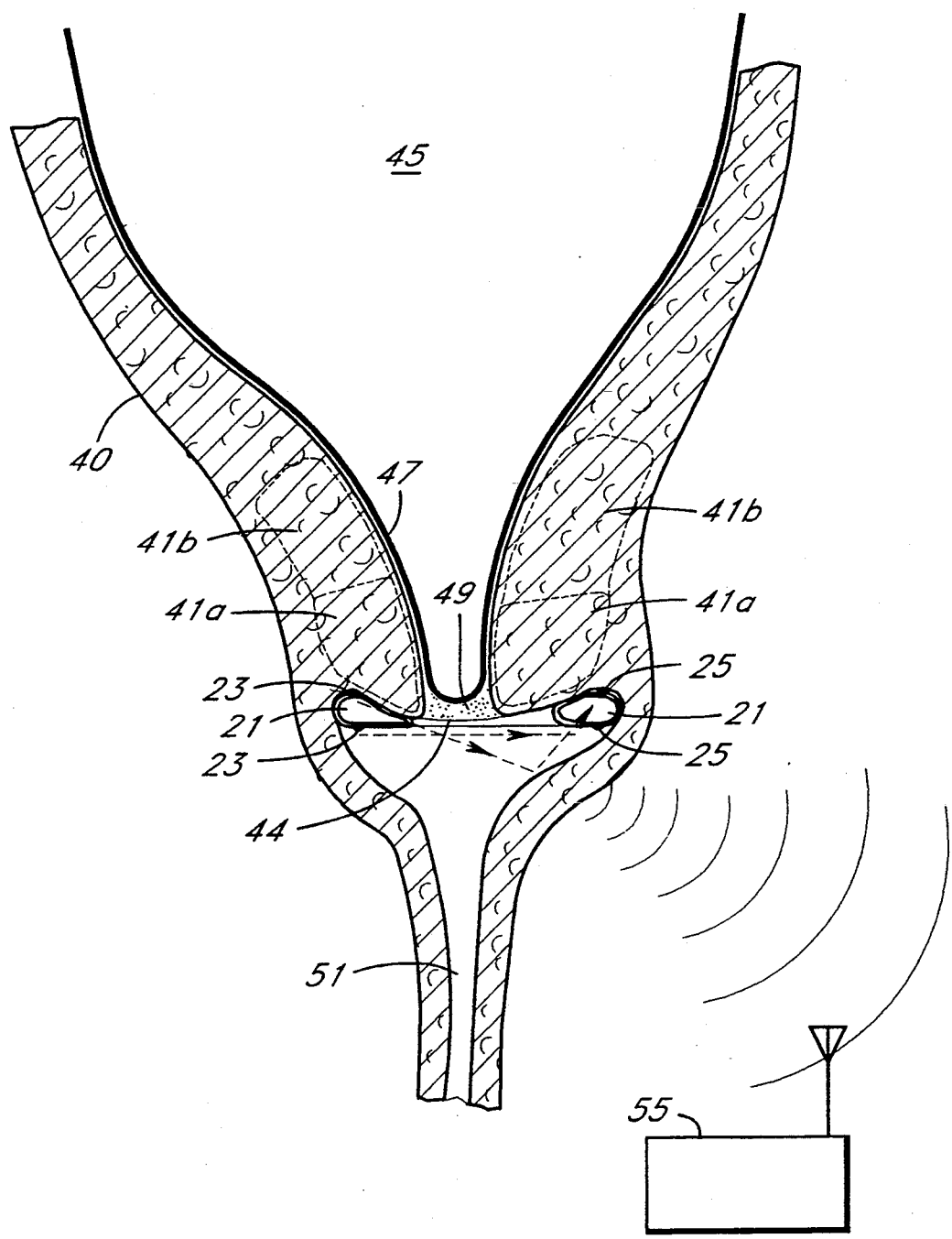
FIG. 6 is a side sectional expanded detail of the female uterus and cervix, as was shown in FIG. 4, but illustrating an advanced stage of premature labor.
Figure 2:
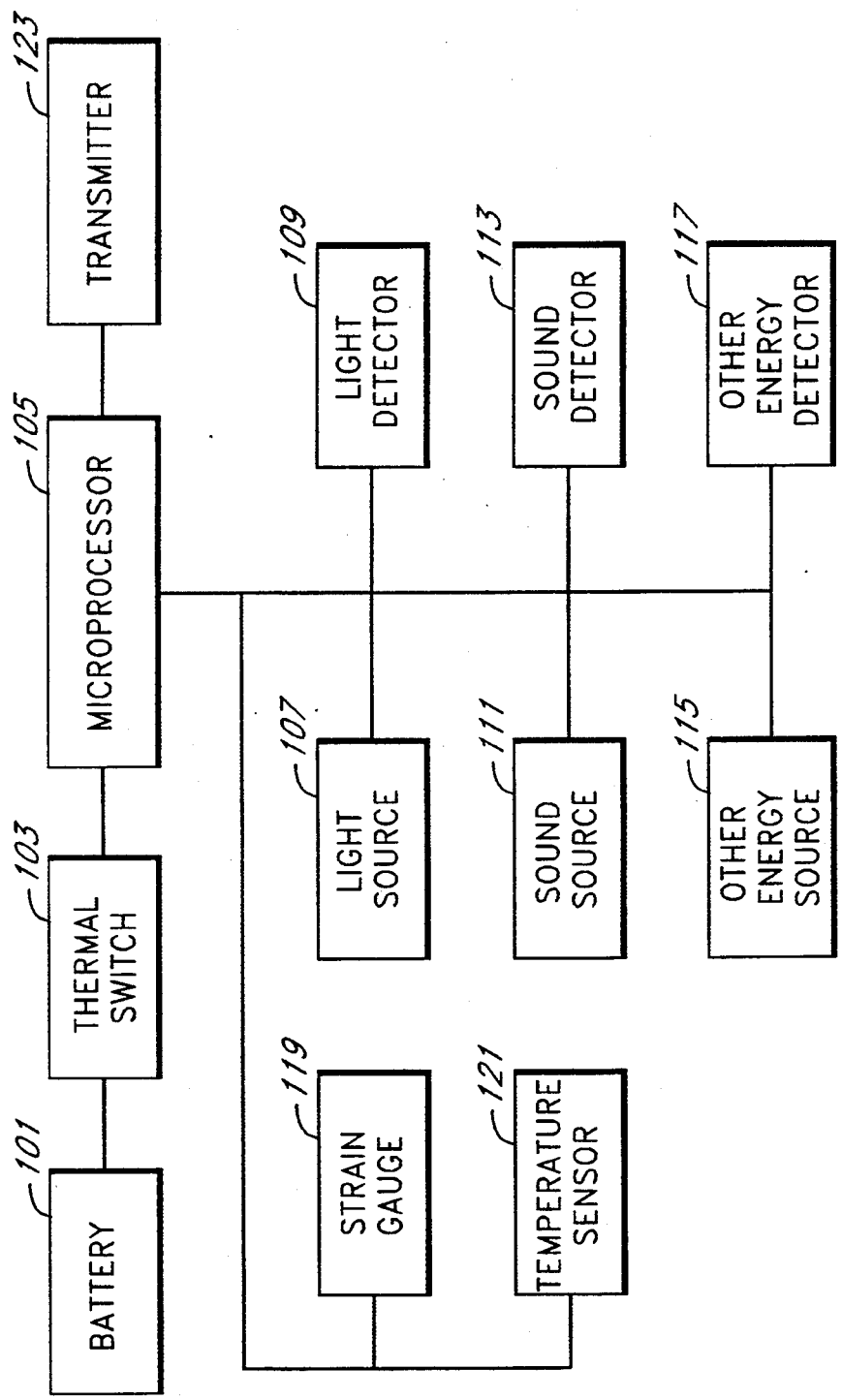

Referring to FIG. 6, a depiction with a perspective similar to that shown in FIGS. 4 and 5 is shown to illustrate the state of the cervix 41 and uterus 40 as it would appear as the premature labor had proceeded to a time when it may be too late to reverse the premature labor. At this stage, the membrane sac 47 is protruding through and almost even with the lower extremity of the un-stretched cervical tissue 41a. The mucus plug 49 has been nearly completely expelled for the most part, with only a small amount of it remaining. The membrane sac 47 is in a position where it is about to rupture.

Note that, even though the conditions in FIG. 6 are extremely changed from those in FIG. 5, that the gradual nature of the change is readily detected by the electronic components in the pessary 21. In FIG. 6, the energy from the energy emitter 23 falls directly on the detector 25. In the case of light, the light would be directly picked up by the detector 25. The stages of premature labor leading up to the extreme condition shown in FIG. 6 would produce a gradual lessening of the mass of tissue and blood perfusion within the internal confines of the pessary 21. This lessening of the mass and blood perfusion between the energy emitter 23 falls and the detector 25 can be measured and correlated to the timing of the labor process.

For example, the energy received by the detector 25 will probably not vary linearly with the linear displacement of the cervix 41 tissue mass, but may follow some other function. This other function may be programmed into a microchip, such as microchip 29 within the pessary, but more likely into a microprocessor in the patient monitor unit 55. In this manner, a correlation may be obtained, and a direct readout of the progression of the premature pregnancy. Further, the progression can be geared to specific stages of the pregnancy. The physician, especially if communicating telephonically, may be able to make decisions based upon the milestones in the premature labor process which could be indicated on the patient monitor unit 55 or estimated from a mathematically linearized process of premature labor indicator. Such an indicator may be given in terms of percent, or a number scale, or specific stages.

Referring to FIG. 7, a schematic block diagram of one possible configuration for the system of the present invention is shown. A battery 101 supplies power to a thermal switch 103. Thermal switch 103 will allow power to flow to a microprocessor 105 if the temperature is sufficiently high, approximating that of the human body. The microprocessor 105 communicates with pairs of energy emitters 23/detectors 25 which were previously described, but which are labeled and shown for greater detail in FIG. 7.

A light source 107 is controlled by microprocessor 105 while a light detector 109 senses the light produced by light source 107 and communicates a signal representative of the detected light to the microprocessor 105. A sound source 111 is controlled by microprocessor 105 while a sound detector 113 senses the sound produced by sound source 111 and communicates a signal representative of the detected sound to the microprocessor 105. Also shown is a generalized emitter/detector pair illustrated as an other energy source 115 controlled by microprocessor 105 while an other energy detector 117 senses the other energy produced by the other energy source 115 and communicates a signal representative of the other energy detected to the microprocessor 105.

Other inputs to the microprocessor 105 may be passive, such as a strain gauge 119 and a temperature sensor 121. A transmitter 123 is controlled by microprocessor 105 and is used to send signals to the patient monitor unit 55 shown in the previous Figures. It is clear here that microprocessor 105 can control the timing of the various connected blocks. Microprocessor can determine when light, sound or other energy source emits its energy, when passive sensors are to be activated, and more importantly when the transmitter is to send such information to the patient monitor unit 55 shown in the previous Figures.

While the present invention has been described in terms of a personal electronics directory, one skilled in the art will realize that the structure and techniques of the present invention can be applied to many appliances. The present invention may be applied in any situation where a computer chip needs to be accessed quickly, without the need for a technician, and without any special tools.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed:

1. A premature labor monitor system comprising:
   means for transmitting energy through at least a portion of the cervix and which energy's propagation through tissue of said portion of the cervix changes during the stages of premature labor;
   detector means for detecting energy which has been transmitted through said tissue of said cervix;
   transmission means, connected to said detector means, for receiving a first signal representative of said detected energy and transmitting a second signal associated with said detected energy, patient monitor means for receiving said second signal from said transmission means and for providing indications based upon said second signal, wherein said transmission means further comprises:
   a first interface connected to said detector means;
   an electromagnetic transmitter connected to said interface;
   an electromagnetic receiver, capable of receiving electromagnetic transmissions from said electromagnetic transmitter; and
   a second interface connected to said electromagnetic receiver and to said patient monitor means.

2. The monitor system recited in claim 1 wherein said means for transmitting energy, said detector means for detecting energy, and said transmission means are commonly supported.

3. The monitor system recited in claim 1 wherein said transmission means is also for determining the onset of premature birth based upon said first signal representative of said detected energy and wherein said second signal is an alarm signal warning of the onset of premature birth.

4. The monitor system recited in claim 1 wherein said second signal is indicative of said detected energy and where said patient monitor means is also for determining the onset of premature birth based upon said second signal received.

5. The monitor system recited in claim 1 further comprising a pessary and wherein said means for transmitting energy, said detector means for detecting energy, said first interface, and said electromagnetic transmitter are all supported by said pessary.

6. A premature labor monitor system comprising:
means for transmitting energy through at least a portion of the cervix and which energy's propagation through tissue of said portion of the cervix changes during the stages of premature labor;
detector means for detecting energy which has been transmitted through said tissue of said cervix;
transmission means, connected to said detector means, for receiving a first signal representative of said detected energy and transmitting a second signal associated with said detected energy, patient monitor means for receiving said second signal from said transmission means and for providing indications based upon said second signal, wherein said transmission means further comprises:
a first interface connected to said detector means;
at least one conductor having a first end connected to said interface, and a second end; and
a second interface connected to said second end of said at least one conductor and to said patient monitor means.

7. A premature labor monitor system comprising:
means for transmitting energy through at least a portion of the cervix and which energy's propagation through tissue of said portion of the cervix changes during the stages of premature labor;
detector means for detecting energy which has been transmitted through said tissue of said cervix;
transmission means, connected to said detector means, for receiving a first signal representative of said detected energy and transmitting a second signal associated with said detected energy;
patient monitor means for receiving said second signal from said transmission means and for providing indications based upon said second signal; and
a pessary, and wherein said means for transmitting energy, said detector means for detecting energy and said transmission means are all supported by said pessary.

8. The monitor system recited in claim 7 wherein said pessary has the shape of an elongate loop.

9. The monitor system recited in claim 8 wherein an internal surface of said elongate loop includes a frusto-conical shaped surface.

10. The monitor system of claim 7 wherein said pessary is made of smooth flexible material.

11. The monitor system of claim 7 wherein said patient monitor means is also for interpreting whether changes in said detected energy based upon said transmitted signal are indicative of the onset of premature labor.

12. The monitor system recited in claim 7 where said pessary is in the shape of a frusto-conical annular cylinder and has a diameter of from about fifty millimeters to about ninety millimeters.

13. A process of monitoring premature labor comprising the steps of:
inserting a pessary into the vagina of a pregnant female in a position surrounding the cervical opening;
transmitting energy from said pessary into the tissue of and surrounding said pessary; and
detecting said energy at a detector in said pessary;
transmitting a signal indicative of premature labor, based upon said detected energy, to a patient monitor.

14. The process of monitoring premature labor as recited in claim 13 wherein said transmitting a signal step is performed by using electromagnetic signals transmitted through the body of said pregnant female.

15. The process of monitoring premature labor as recited in claim 13 wherein said transmitting a signal step is performed using electrical conductors.

* * * * *